United States Patent
Jousseaume et al.

(10) Patent No.: US 8,338,336 B2
(45) Date of Patent: Dec. 25, 2012

(54) SYNERGISTIC HERBICIDAL COMPOSITION CONTAINING PENOXSULAM AND OXYFLUORFEN

(75) Inventors: Christian Jousseaume, Vilanova I la Geltru (ES); Salvador Carrasco Campos, Mairena del Aljarafe (ES); Richard K. Mann, Franklin, IN (US); Monica Sorribas Amela, Indianapolis, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 13/014,869

(22) Filed: Jan. 27, 2011

(65) Prior Publication Data

US 2011/0190134 A1     Aug. 4, 2011

Related U.S. Application Data

(60) Provisional application No. 61/229,461, filed on Jan. 29, 2010.

(51) Int. Cl.
*A01N 43/60* (2006.01)
(52) U.S. Cl. ....................................................... 504/136
(58) Field of Classification Search ........................ None
See application file for complete search history.

(56) References Cited

U.S. PATENT DOCUMENTS 5,858,924 A    1/1999  Johnson et al.

FOREIGN PATENT DOCUMENTS

| WO | WO 2004/080171 A2 | 9/2004 |
| WO | WO 2011/094386 | 8/2011 |

OTHER PUBLICATIONS

"Penoxsulam and Its Use as a Herbicide in Mixtures for Use in Rice, Wheat, Barely, Oats, Sorghum, Corn, Maize, Ivm, Rangeland Pastures, Grasslands, Fallowland, Turf, and Aquatics" The IP.com Journal, vol. 5, No. 4, Apr. 2005, pp. 286-293.*
Disclosed Anonymously 462055: "2-(2,2-difluoroethoxy)-6-trifluoromethyl-N-(5,8-dimethoxy[1,2,4]triazolo[1,5-c] pyrimidin-2-yl)benzenesulfonamide and its use as a herbicide in mixtures" Research Disclosure, Oct. 2002, pp. 1832-1833.

* cited by examiner

*Primary Examiner* — Alton Pryor
(74) *Attorney, Agent, or Firm* — Robert Chang

(57) ABSTRACT

Penoxsulam and oxyfluorfen synergistically control weeds in crops, especially perennial tree and vine crops, rice, cereal and grain crops, pastures, rangelands, IVM and turf. Such compositions provide improved pre-emergence residual and post-emergence burndown with residual herbicidal weed control.

10 Claims, No Drawings

SYNERGISTIC HERBICIDAL COMPOSITION CONTAINING PENOXSULAM AND OXYFLUORFEN

CROSS REFERENCE TO RELATED APPLICATIONS

This application claims the benefit of U.S. Provisional Application Ser. No. 61/299,461 filed on 29 Jan. 2010.

FIELD OF THE INVENTION

This invention concerns a synergistic herbicidal composition containing (a) penoxsulam and (b) oxyfluorfen for controlling weeds in crops, especially perennial tree and vine crops, rice, cereal and other broadleaf and grain crops, pastures, rangelands, IVM and turf. These compositions provide improved pre-emergence residual and post-emergence burndown herbicidal weed control.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Eighth Edition, 2002, p. 462 "'synergism' [is] an interaction of two or more factors such that the effect when combined is greater than the predicted effect based on the response to each factor applied separately." The present invention is based on the discovery that penoxsulam and oxyfluorfen, already known individually for their herbicidal efficacy, display a synergistic effect when applied in combination.

The herbicidal compounds forming the synergistic composition of this invention are independently known in the art for their effects on plant growth.

SUMMARY OF THE INVENTION

The present invention concerns a synergistic herbicidal mixture comprising an herbicidally effective amount of (a) penoxsulam and (b) oxyfluorfen. The compositions may also contain an agriculturally acceptable adjuvant and/or carrier, as well as other pesticides.

The present invention also concerns herbicidal compositions for and methods of controlling the growth of undesirable vegetation, particularly in perennial tree and vine crops, as well as monocot crops including rice, wheat, barley, oats, rye, sorghum, corn, maize, pastures, grasslands, rangelands, fallowland, IVM and turf and the use of these synergistic compositions.

The species spectra of penoxsulam and oxyfluorfen, i.e., the weed species which the respective compounds control, are broad and highly complementary. For example, it has been surprisingly found that a combination of penoxsulam and oxyfluorfen exhibits a synergistic action in the control of fleabane (*Conyza bonariensis*, ERIBO), marestail (*Conyza canadensis*, ERICA), mallow/malva (*Malva neglecta*, MALNE), black nightshade (*Solanum nigrum*, SOLNI), purslane (*Portulaca oleracea*, POROL), common lambsquarter (*Chenopodium album*, CHEAL), common heliotrope (*Heliotropium europaeum*, HEOEU), and field madder (*Sherardia arvensis*, SHRAR) at application rates equal to or lower than the rates of the individual compounds. This combination will also control acetolactate synthase-(ALS), glyphosate- and glufosinate-resistant *Conyza* species.

Oxyfluorfen can also be tank mixed preferentially with the following ALS mode of action products for improved weed control: amidosulfuron, azimsulfuron, bensulfuron-methyl, bispyribac-sodium, cinosulfuron, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, halosulfuron-methyl, imazamethabenz-methyl, imazamox, imazapic, imazapyr, imazaquin, imazethapyr, imazosulfuron, mesosulfuron-methyl, metazosulfuron, metsulfuron-methyl, nicosulfuron, orthosulfamuron, oxasulfuron, primisulfuron, procarbazone-sodium, propoxycarbazone, propyrisulfuron, prosulfuron, pyriftalid, pyrazosulfuron-ethyl, pyribenzoxim, pyriminobac-methyl, pyroxsulam, pyrimisulfan, rimsulfuron, sulfometuron-methyl, triasulfuron, tribenuron-methyl, triflusulfuron-methyl and tritosulfuron.

Penoxsulam can also be tank mixed preferentially with the following PPO (protoporphyrinogen oxidase inhibitors) mode of action products for improved weed control: azafenidin, bifenox, butafenacil, carfentrazone-ethyl, cinidon-ethyl, flumiclorac-pentyl, flumioxazin, fomesafen, oxadiargyl, oxadiazinon, pentoxazone, pyraclonil, pyraflufen-ethyl, saflufenacil and sulfentrazone.

DETAILED DESCRIPTION OF THE INVENTION

Penoxsulam is the common name for 2-(2,2-difluoroethoxy)-N-(5,8-dimethoxy-[1,2,4]triazolo[1,5-c]pyrimidin-2-yl)-6-(trifluoromethyl)benzenesulfonamide. Its herbicidal activity is described in *The Pesticide Manual*, Fourteenth Edition, 2006. Penoxsulam controls *Echinochloa* spp., as well as many broadleaf and sedge weeds in rice, sorghum, perennial tree and vine crops, and *Apera* spp. grass as well as many broadleaf weeds in cereals.

Oxyfluorfen is the common name for 2-chloro-1-(3-ethoxy-4-nitrophenoxy)-4-trifluoromethyl)benzene. Its herbicidal activity is described in *The Pesticide Manual*, Fourteenth Edition, 2006. Oxyfluorfen controls a wide range of economically important broadleaf and grass weeds in perennial tree and vine crops, sunflower and vegetables.

The term herbicide is used herein to mean an active ingredient that kills, controls or otherwise adversely modifies the growth of plants. An herbicidally effective or vegetation controlling amount is an amount of active ingredient which causes an adverse modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention pre-emergence prior to germination and emergence, or post-emergence to relatively immature undesirable vegetation, to achieve the maximum control of weeds.

In the composition of this invention, the weight ratio of penoxsulam to oxyfluorfen at which the herbicidal effect is synergistic lies within the range of between about 1:560 and about 1.33:1.0.

The rate at which the synergistic composition is applied will depend upon the particular type of weed to be controlled, the degree of control required, the length of control required, and the timing and method of application. In general, the composition of the invention can be applied at an application rate of between about 79 grams active ingredient per hectare (g/ha) and about 2340 g/ha based on the total amount of active ingredients in the composition. Penoxsulam is applied at a rate between about 4 g/ha and about 100 g/ha and oxyfluorfen is applied at a rate between about 75 g/ha and about 2240 g/ha. Penoxsulam is preferentially applied at a rate between 5 g/ha and 50 g/ha and oxyfluorfen is preferentially applied at a rate between 100 g/ha and 2240 g/ha.

The components of the synergistic mixture of the present invention can be applied either separately or as part of a multipart herbicidal system, which can be provided as a pre-mix or a tank mix.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 4-CPA, 4-CPB, 4-CPP, 2,4-D, 3,4-DA, 2,4-DB, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, parafluoron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

The synergistic composition of the present invention can, further, be used in conjunction with glyphosate, glufosinate, dicamba, imidazolinones, sulfonylureas, or 2,4-D on glyphosate-tolerant, glufosinate-tolerant, dicamba-tolerant, imidazolinone-tolerant, sulfonylurea-tolerant and 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, cyprosulfamate, daimuron, dichlormid, dicyclonon, diethlate, dimepiperate, disulfoton, fenchlorazole-ethyl, fenclorim, flurazole, fluxofenim, furilazole, harpin proteins, isoxadifen-ethyl, mefenpyr-diethyl, mephenate, MG 191, MON 4660, naphthalic anhydride (NA), oxabetrinil, R29148 and N-phenyl-sulfonylbenzoic acid amides, to enhance their selectivity.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO) and PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like.

The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 1 to 98 weight percent, preferably 10 to 90 weight percent. Such compositions are typically diluted with an inert carrier, such as water, before application. The diluted compositions usually applied pre-emergence or post-emergence to weeds or the locus of weeds generally contain 0.0001 to 10 weight percent active ingredient and preferably contain 0.001 to 5.0 weight percent.

The present compositions can be applied to weeds or their locus by the use of conventional ground or aerial dusters, sprayers, and granule applicators, and by other conventional means known to those skilled in the art.

The following examples illustrate the present invention.

Evaluation of Pre-Emergence and Post-Emergence Herbicidal Activity of Mixtures in the Field Field trials were conducted in perennial tree and vine crops using standard herbicide small plot research methodology. Plots varied from 3×3 meter (m) to 3×10 m (width×length) with 3 to 4 replicates per treatment. The perennial tree and vine crops were grown using normal cultural practices for the respective areas for the trials, using normal planting, fertilization, watering, flooding and maintenance for pests to ensure good growth of the crop and the weeds.

All treatments in the field trials were applied using a carbon dioxide ($CO_2$) backpack sprayer calibrated to apply 187 liters per hectare (L/ha) spray volume. Commercially available products of penoxsulam and oxyfluorfen were mixed in water at appropriate formulated product rates to achieve the desired rates shown based on a unit area of application (hectare). Treatments were rated at different intervals from treatment to evaluation, from 7 to 175 days after application as compared to the untreated control plants. Due to the long term residual weed control needed to determine the synergistic effect, all single entity products and their tank mixes were mixed with glyphosate to ensure complete weed burndown to be able to measure residual weed control and not just burndown of weeds. Visual weed control was scored on a scale of 0 to 100 percent where 0 corresponds to no injury and 100 corresponds to complete kill.

Tables 1 to 3 demonstrate the synergistic herbicidal efficacy of penoxsulam+oxyfluorfen tank mixes for pre-emergence residual weed control. Table 4 demonstrates the synergistic herbicidal post-emergence activity of penoxsulam+oxyfluorfen. All treatment results are an average of 3 to 4 replicates and the tank mix interactions demonstrate a positive, synergistic interaction according to Colby's equation.

Colby's equation was used to determine the herbicidal effects expected from the mixtures (Colby, S. R. Calculation of the synergistic and antagonistic response of herbicide combinations. *Weeds* 1967, 15, 20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 1 to 4.

TABLE 1

Synergistic Herbicidal Activity from winter pre-emergence applications on residual broadleaf weed control in the field when rated 50 to 132 Days After Application.
% Control

| Application Rate (g/ha) | | ERIBO | | ERICA | | MALNE | |
|---|---|---|---|---|---|---|---|
| Penoxsulam | Oxyfluorfen | Ob | Ex* | Ob | Ex* | Ob | Ex* |
| 8.8 | 0 | 65 | — | — | — | — | — |
| 0 | 1120 | 0 | — | — | — | — | — |
| 8.8 | 1120 | 96 | 65 | — | — | — | — |
| 8.8 | 0 | — | — | 75 | — | — | — |
| 0 | 1680 | — | — | 5 | — | — | — |
| 8.8 | 1680 | — | — | 100 | 76 | — | — |
| 17.5 | 0 | — | — | — | — | 37 | — |
| 0 | 1680 | — | — | — | — | 30 | — |
| 17.5 | 1680 | — | — | — | — | 100 | 56 |
| 35 | 0 | — | — | — | — | 50 | — |
| 0 | 1680 | — | — | — | — | 30 | — |
| 35 | 1680 | — | — | — | — | 98 | 65 |

ERIBO = fleabane (*Conyza bonariensis*)
ERICA = marestail (*Conyza canadensis*)
MALNE = mallow/malva (*Malva neglecta*)
Ob = Observed visual weed control
Ex* = Expected weed control as defined by Colby Equation

TABLE 2

Synergistic Herbicidal Activity from autumn pre-emergence applications on residual broadleaf weed control in the field when rated 97 to 175 Days After Application.
% Control

| Application Rate (g/ha) | | ERICA (1) | | ERICA (2) | | SHRAR | |
|---|---|---|---|---|---|---|---|
| Penoxsulam | Oxyfluorfen | Ob | Ex* | Ob | Ex* | Ob | Ex* |
| 20 | 0 | 23 | — | 6 | — | 0 | — |
| 0 | 150 | 38 | — | 79 | — | 63 | — |
| 20 | 150 | 93 | 52 | 96 | 80 | 98 | 63 |

SHRAR = field madder (*Sherardia arvensis*)
ERICA = marestail (*Conyza canadensis*)
Ob = Observed visual weed control
Ex* = Expected weed control as defined by Colby Equation
(1) = Utrera, Spain
(2) = Moron de la frontera, Spain

TABLE 3

Synergistic Herbicidal Activity from autumn post-emergence applications on residual broadleaf weed control in the field when rated 56 Days After Application.
% Control

| Application Rate (g/ha) | | POROL | | CHEAL | | HEOEU | |
|---|---|---|---|---|---|---|---|
| Penoxsulam | Oxyfluorfen | Ob | Ex* | Ob | Ex* | Ob | Ex* |
| 20 | 0 | 0 | — | 0 | — | 0 | — |
| 0 | 150 | 0 | — | 0 | — | 0 | — |
| 20 | 150 | 50 | 0 | 97 | 0 | 67 | 0 |

POROL = purslane (*Portulaca oleracea*)
CHEAL = common lambsquarter (*Chenopodium album*)
HEOEU = common heliotrope (*Heliotropium europaeum*)
Ob = Observed visual weed control
Ex* = Expected weed control as defined by Colby Equation

TABLE 4

Synergistic Herbicidal Activity from autumn post-emergence applications on the post-emergence burndown activity on broadleaf weed control in the field when rated 7 to 20 Days After Application.
% Control

| Application Rate (g/ha) | | SOLNI(1) | | SOLNI(2) | |
|---|---|---|---|---|---|
| Penoxsulam | Oxyfluorfen | Ob | Ex* | Ob | Ex* |
| 20 | 0 | 10 | — | 10 | — |
| 0 | 150 | 35 | — | 45 | — |
| 20 | 150 | 90 | 42 | 90 | 51 |

SOLNI = black nightshade (*Solanum nigrum*)
Ob = Observed visual weed control
Ex* = Expected weed control as defined by Colby Equation
(1) = Seville, Spain - 20 Days After Application
(2) = Seville, Spain - 7 Days After Application

What is claimed is:

1. A synergistic herbicidal mixture comprising a herbicidally effective amount of (a) penoxsulam and (b) oxyfluorfen, wherein the weight ratio of penoxsulam to oxyfluorfen is 1:7.5 to 1:191.

2. A herbicidal composition comprising a herbicidally effective amount of the synergistic herbicidal mixture of claim 1 and an agriculturally acceptable adjuvant and/or carrier.

3. A method of controlling undesirable vegetation which comprises contacting the vegetation or the locus thereof with or applying to the soil to prevent the emergence or growth of vegetation a herbicidally effective amount of the synergistic herbicidal mixture of claim 1.

4. The method of claim 3, wherein the undesirable vegetation is controlled in crops.

5. The method of claim 4, wherein the undesirable vegetation is controlled in perennial tree, vine crops, cereal crops, grain crops, pastures, rangelands, or industrial vegetation management.

6. The method of claim 4, wherein the undesirable vegetation is controlled in tree crops or vine crops.

7. The method of claim 4, wherein the undesirable vegetation is fleabane, marestail, malva, field madder, purslane, common lambsquarter, common heliotrope, or black nightshade.

8. The method of claim 3, wherein the synergistic herbicidal mixture is applied at an application rate of between about 79 g/ha and about 2340 g/ha based on the total amount of penoxsulam and oxyfluorfen.

9. The method of claim 8, wherein penoxsulam is applied at a rate of about 4 g/ha to 100 g/ha and oxyfluorfen is applied at a rate of between about 75 g/ha and about 2240 g/ha.

10. The method of claim 9, wherein penoxsulam is applied at a rate of about 5 g/ha and 50 g/ha and oxyfluorfen is applied at a rate of about 100 g/ha and 2240 g/ha.

* * * * *

UNITED STATES PATENT AND TRADEMARK OFFICE
CERTIFICATE OF CORRECTION

PATENT NO. : 8,338,336 B2  
APPLICATION NO. : 13/014869  
DATED : December 25, 2012  
INVENTOR(S) : Jousseaume et al.

Page 1 of 1

It is certified that error appears in the above-identified patent and that said Letters Patent is hereby corrected as shown below:

In column 10, line 24 (part of claim 10), insert the term -- between -- before the term "about" to read:

-- at a rate of between about 5 g/ha and 50 g/ha --.

In column 10, line 25 (part of claim 10), insert the term -- between -- before the term "about" to read:

-- at a rate of between about 100 g/ha and 2240 g/ha. --.

Signed and Sealed this  
Twelfth Day of February, 2013

Teresa Stanek Rea  
*Acting Director of the United States Patent and Trademark Office*